(12) United States Patent
Widly

(10) Patent No.: US 12,257,585 B2
(45) Date of Patent: *Mar. 25, 2025

(54) COMPONENTS AND KITS FOR COLLECTING, SECURING, IDENTIFYING AND TRACKING UNIQUE SAMPLES

(71) Applicant: DriverFacts Inc., Anaheim, CA (US)

(72) Inventor: David Widly, Anaheim, CA (US)

(73) Assignee: DriverFacts Inc., Anaheim, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/527,260

(22) Filed: Dec. 2, 2023

(65) Prior Publication Data
US 2024/0123451 A1    Apr. 18, 2024

Related U.S. Application Data

(63) Continuation of application No. 16/809,512, filed on Mar. 4, 2020, now Pat. No. 11,833,518.

(60) Provisional application No. 62/869,419, filed on Jul. 1, 2019, provisional application No. 62/813,485, filed on Mar. 4, 2019.

(51) Int. Cl.
*B01L 3/00*     (2006.01)
*A01N 1/02*     (2006.01)

(52) U.S. Cl.
CPC ............ *B01L 3/545* (2013.01); *A01N 1/0242* (2013.01); *B01L 3/508* (2013.01); *B01L 2300/021* (2013.01)

(58) Field of Classification Search
CPC .............. A01N 1/0242; A61B 10/0096; A61B 10/0038; A61B 10/0045; B01L 3/545; B01L 3/508; B01L 3/50
USPC ......................................... 206/569, 223, 216
See application file for complete search history.

(56) References Cited

U.S. PATENT DOCUMENTS

2006/0060494 A1*  3/2006  Goodman ........ A61B 5/150305
                                                        604/408
2020/0254442 A1*  8/2020  Nagy ................. A61B 10/0096

* cited by examiner

*Primary Examiner* — Edwyn Labaze
(74) *Attorney, Agent, or Firm* — UltimatEdge IP Law Group, P.C.; Dean G. Stathakis

(57) ABSTRACT

The present specification discloses collection kits for collecting a biological sample being handled by a chain-of-custody protocol and methods and uses for collecting a sample using such collection kits. In some aspects, a collection kit disclosed herein can comprise one or more identification labels, a sample collection device, one or more sample containers, and a collecting pouch. In some aspects, a collection kit disclosed herein can comprise one or more sample containers, a sample shipping container, one or more identification labels, and a collecting pouch.

20 Claims, 9 Drawing Sheets

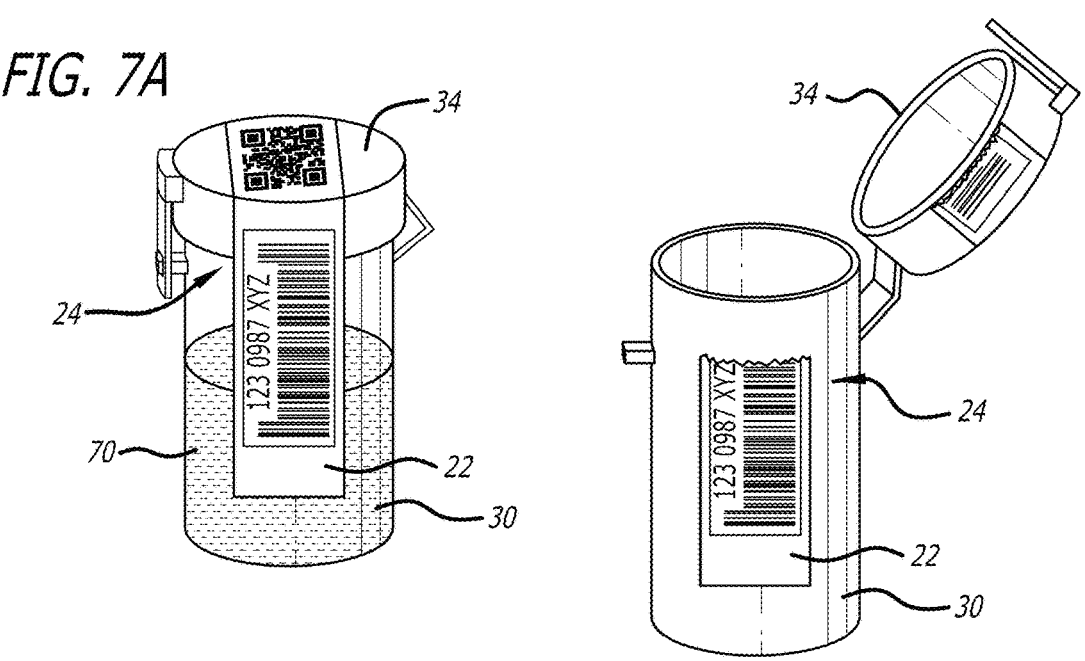
FIG. 7A
FIG. 7B
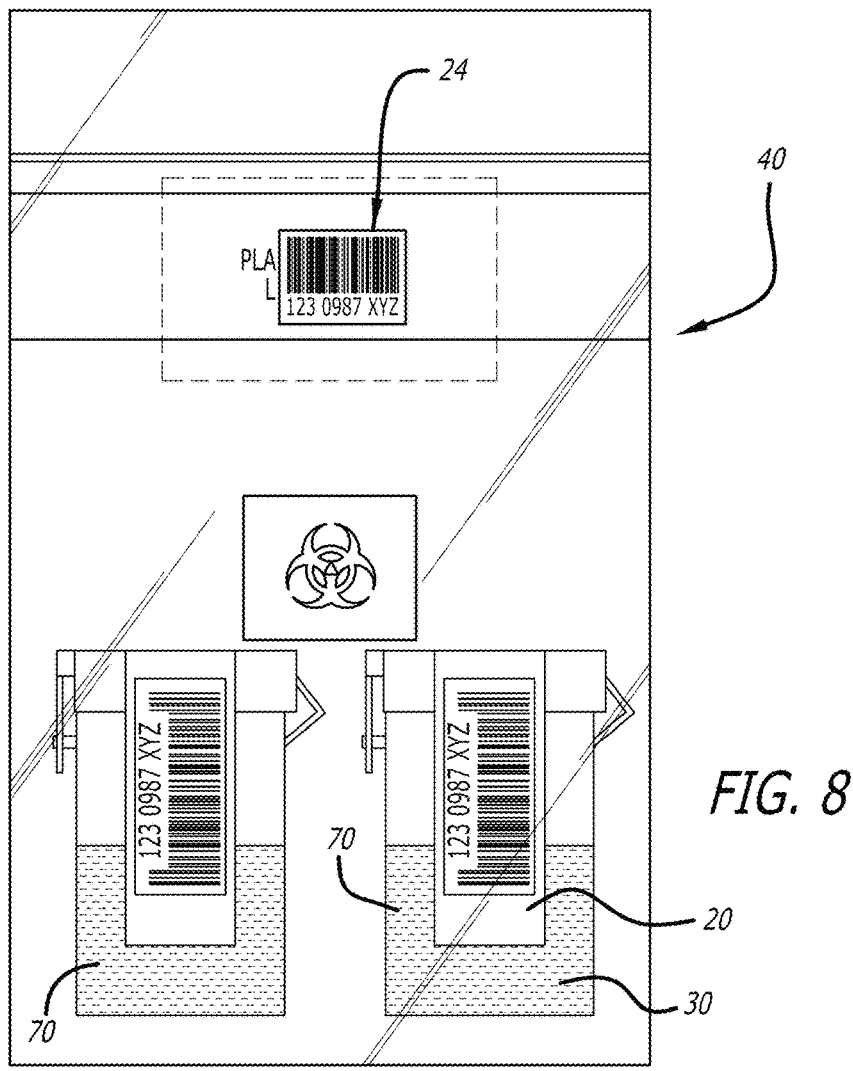
FIG. 8

COMPONENTS AND KITS FOR COLLECTING, SECURING, IDENTIFYING AND TRACKING UNIQUE SAMPLES

This application is a continuation that claims the benefit of priority and is entitled to the filing date pursuant to 35 U.S.C. § 120 of U.S. Non-Provisional patent application Ser. No. 16/809,512, filed Mar. 4, 2020, a 35 U.S.C. § 111 patent application which claims the benefit of priority and is entitled to the filing date pursuant to 35 U.S.C. § 119(e) of U.S. Provisional Patent Application 62/869,419, filed Jul. 1, 2019 and U.S. Provisional Patent Application 62/813,485, filed Mar. 4, 2019, the content of each of which is hereby incorporated by reference in its entirety.

Chain-of-custody (CoC) is a record that chronologically documents the sequence of procurement, custody, control, transfer, analysis, disposition, management and storage of physical and/or electronic evidence. This procedure requires clear, complete and concise information of a sample, each person who handled the sample, and the results obtained from analyzing the sample for the entire phase of testing, from the moment an individual provides a sample to a collector to the final destination of the sample and the review and reporting of the final test result.

Whether mandated by legal regulations or enacted as a best practice procedure, one of the main purposes of tracking a sample using a CoC protocol is to protect the integrity of the sample. For example, there are many circumstances that may lead to drug testing including pre-employment evaluation, work-related assessment, college or professional athletic monitoring, post-accident investigations, and safety-related appraisals. As a positive drug test result for a controlled substance has adverse consequences for the subject it is imperative that strict chain-of-custody (CoC) practices and standards are in place to prevent adulteration or contamination of a biological sample. Similarly, during investigation of a crime scene, evidence is routinely collected in an effort to elucidate what happened and help apprehend the person or persons responsible for the crime. Strict chain-of-custody (CoC) practices of biological and/or non-biological samples collected at a crime scene is essential to ensure that such evidence can be authenticated and used in a court of law in order to help determine the guilt or innocence of a person accused of the crime. CoC protocols are also useful regarding the collection of samples for scientific research ranging from pharmaceutical drug development to archeological investigation, ecological and environmental evaluations of pollutants, or any other situation where complete information regarding the collection, transportation and analysis of a sample is desired.

The problems associated with current CoC protocols can be exemplified using random drug testing policies as a non-limiting example. Due to concerns of public safety regarding illegal drug use in the workplace, random drug testing is becoming more prevalent in our society. Currently, such testing is mandated by the federal government in many industrial sectors such as transportation, law enforcement and the military. For example, Department of Transportation (DOT) mandates that all companies governed by 49 C.F.R. Part 40 randomly test all safety-sensitive employees for drug and alcohol use. Typically, an employee is informed upon his arrival at work that he/she was randomly selected for drug testing. A sample is immediately collected at his/her place of employment. When the sample being collected is urine, the sample is collected in the presence of another company employee hired to perform this duty (i.e., a collector). Usually, the collection is performed in a lavatory facility on-site. The employee follows the provided instructions and ultimately aliquots the sample from a collection container into two testing containers. Besides observing the collection of the sample, the collector will also record information necessary for the proper testing of the sample and oversee the transportation of the testing containers containing the sample to a testing facility.

Currently there are various ways a collector record information on an employee being drug tested. In one in particular, the collector will use a five-part, carbon copy CoC form and writes all required information on this form. Besides identifying information on the employee, this form also indicates the type of testing to be performed including the substances to be tested. This CoC form also includes a duplicate bar code label for tracking purposes. The collector will peel off one of the bar code labels and affix to one of the testing containers and then take the second label and affix to the second testing container. Once the CoC form is completed and the containers labeled with the bar code, the collector will package up the material and send to a laboratory testing facility for analysis.

In another approach, the collector will manually enter the required information regarding the employee and testing requirements into a software program that will store and send the recorded information electronically to the laboratory testing facility. This software also generated a duplicate bar code label which is printed on standard sheet or labels at the place where the sample for testing is collected. Once printed, the bar code labels are affixed to both testing containers as described above. The collector will package up the containers and send to a laboratory testing facility for analysis.

There are several problems associated with the current CoC procedures. For example, use of the five-part, carbon copy CoC form is cumbersome and time consuming, involves great expense to print and ship to a company, and uses company resources to store and manage the forms. Similarly, current software application require the bar code label to be printed separately, which for CoC requirements must be done at the site of collection. This is commonly a general-purpose lavatory used by all employees. Such an awkward arrangement leads to chronic malfunction of the printer, disruptions due to paper or ink shortages, and uneasiness of the employee, the collector and other co-workers.

As such, new kits and methods are needed that address the shortcomings discussed above as well as improve the accuracy and efficiency of the current CoC procedures

SUMMARY

The present specification discloses a collection container, a collection kit and methods associated with each that addresses the above problems as well as others known in the field and increases the integrity of the CoC procedure ensuring the fidelity of a sample and more accurate and valid test results. In addition, the disclosed collection container, collection kit and associated methods improve the collection and handling of any sample that is difficult to handle due to the composition of the sample or due to require safety precautions make it difficult to handle the sample.

Aspects of the present specification discloses a kit for collecting a sample. The disclosed collection kit comprises an identification label. The collection kit may also contain a sample collection device, one or more sample containers, a collecting pouch, instructions pertaining to the use of the kit and/or collection of the sample, a cleaning wipe, or any combination thereof.

Aspects of the present specification discloses a sample container for a sample. The disclosed sample container comprises an identification label. In aspects, the identification label has a portion associated with the sample container, preferably a lid and one or more portions unassociated with the sample container. The one or more unassociated portions have the adhesive side of the identification label covered with a protective covering that optionally comprises tabs for easy removal. Once a sample is dispensed into the sample container, the lid is secured, the protective covering of the one or more unassociated portions of the identification label are removed, and the one or more unassociated portions are secured to the side of the sample container.

Other aspects of the present specification disclose a method or use for collecting a sample. The disclosed method comprising collecting a sample using a collection kit disclosed herein and affixing a machine readable provided by the disclosed kit to each of the one or more sample containers comprising a sample. The method can also include associating information on the originating source of the sample and/or testing instructions with the identification label.

BRIEF DESCRIPTION OF DRAWINGS

FIG. 3B showing a front perspective view of sample container 30 with lid 34 open.

FIG. 4B showing top plan view of identification label 20 illustrating label side 22 with two different machine-readable codes 24; FIG. 4C showing bottom plan view of identification label 20 illustrating adhesive side 26 with protective covering 28 and tab 29; FIG. 4D showing side elevational view of identification label 20; FIG. 4E showing top plan view of identification label 20 secured to lid 34; FIG. 4F showing bottom plan view of identification label 20 secured to lid 34; and FIG. 4G showing side elevational view of identification label 20 secured to lid 34.

FIGS. 7A-B show an exemplary embodiment of a sample container 30 disclosed herein with FIG. 7A showing a front perspective view of sample container 30 with lid 34 closed and identification label 20 affixed; FIG. 7B showing a front perspective view of sample container 30 with lid 34 open and identification label 20 torn to indicate lid 34 was opened.

FIG. 8 shows an exemplary embodiment of a sealed collecting pouch 40 disclosed herein containing two sample containers 30 each affixed with an identification label 20.

FIG. 10B showing view of back side elevational view of sample shipping container 80.

FIG. 11B showing a top view of sample container 130 with a sample.

DETAILED DESCRIPTION

The present specification discloses a kit for collecting a sample comprises one or more components. In one embodiment, a collection kit disclosed herein can include one or more identification labels and one or more sample containers. In another embodiment, a collection kit disclosed herein can include one or more identification labels, one or more sample containers, and a sample collection device. In another embodiment, a collection kit disclosed herein can include one or more identification labels, one or more sample containers, and a sample shipping container. A collection kit disclosed herein may also include a collecting pouch. A collection kit disclosed herein may also include instructions pertaining to the use of the kit, instructions pertaining to the collection of the sample, or both. Such instructions can be provided together or provided as separate instructions. Additionally, a collection kit disclosed herein can contain a cleaning wipe.

Figure 1:
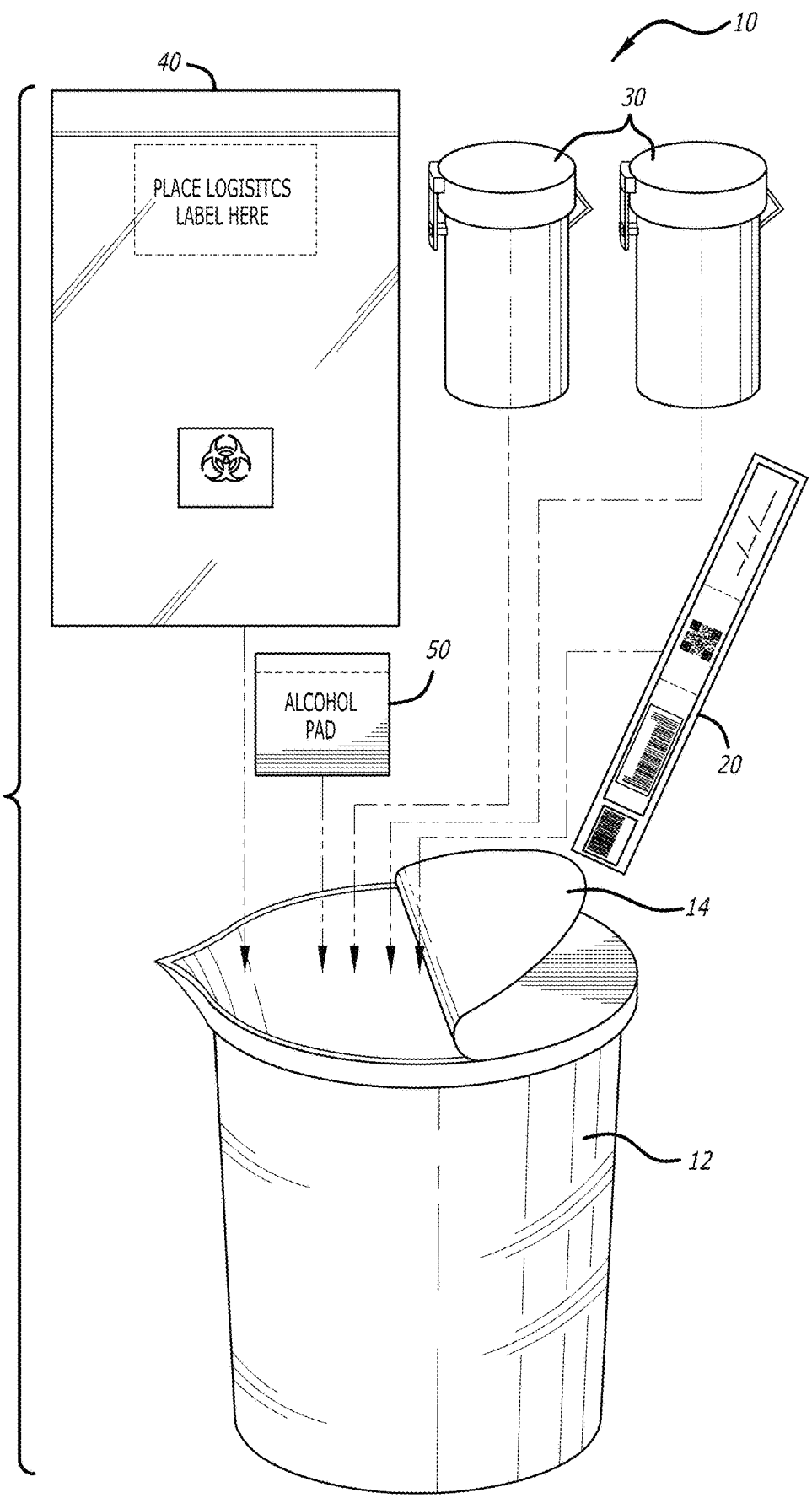
FIG. 1 shows an exemplary embodiment of a collection kit 10 disclosed herein.

In an embodiment, a collection kit disclosed herein is assembled so that the sample collection device servers as a container for the remaining components of the kit. In aspects of this embodiment, and referring to FIG. 1, a collection kit 10 comprises a sample collection device 12 which serves as a container and one or more identification labels 20. In other aspects of this embodiment, a collection kit 10 comprises a sample collection device 12 which serves as a container and one or more identification labels 20 and one or more sample containers 30. In yet other aspects of this embodiment, a collection kit 10 comprises a sample collection device 12 which serves as a container and one or more identification labels 20, one or more sample containers 30 and a collecting pouch 40. In still other aspects of this embodiment, a collection kit 10 comprises a sample collection device 12 which serves as a container and one or more identification labels 20, one or more sample containers 30, a collecting pouch 40 and instructions. In further aspects of this embodiment, a collection kit 10 comprises a sample collection device 12 which serves as a container and one or more identification labels 20, one or more sample containers 30, a collecting pouch 40, instructions and a cleaning wipe 50. In some embodiments, sample collection device 12 is secured in a manner to prevent the other components from falling out or being removed until needed, such as by employing a plastic lid, a seal like an aluminum foil seal or a plastic seal, or other covering. For example, FIG. 1 shows a seal 14 (partially pulled away in this illustration) used to seal sample collection device 12 in a manner that prevents the other components from falling out or being removed until needed.

Figure 9:
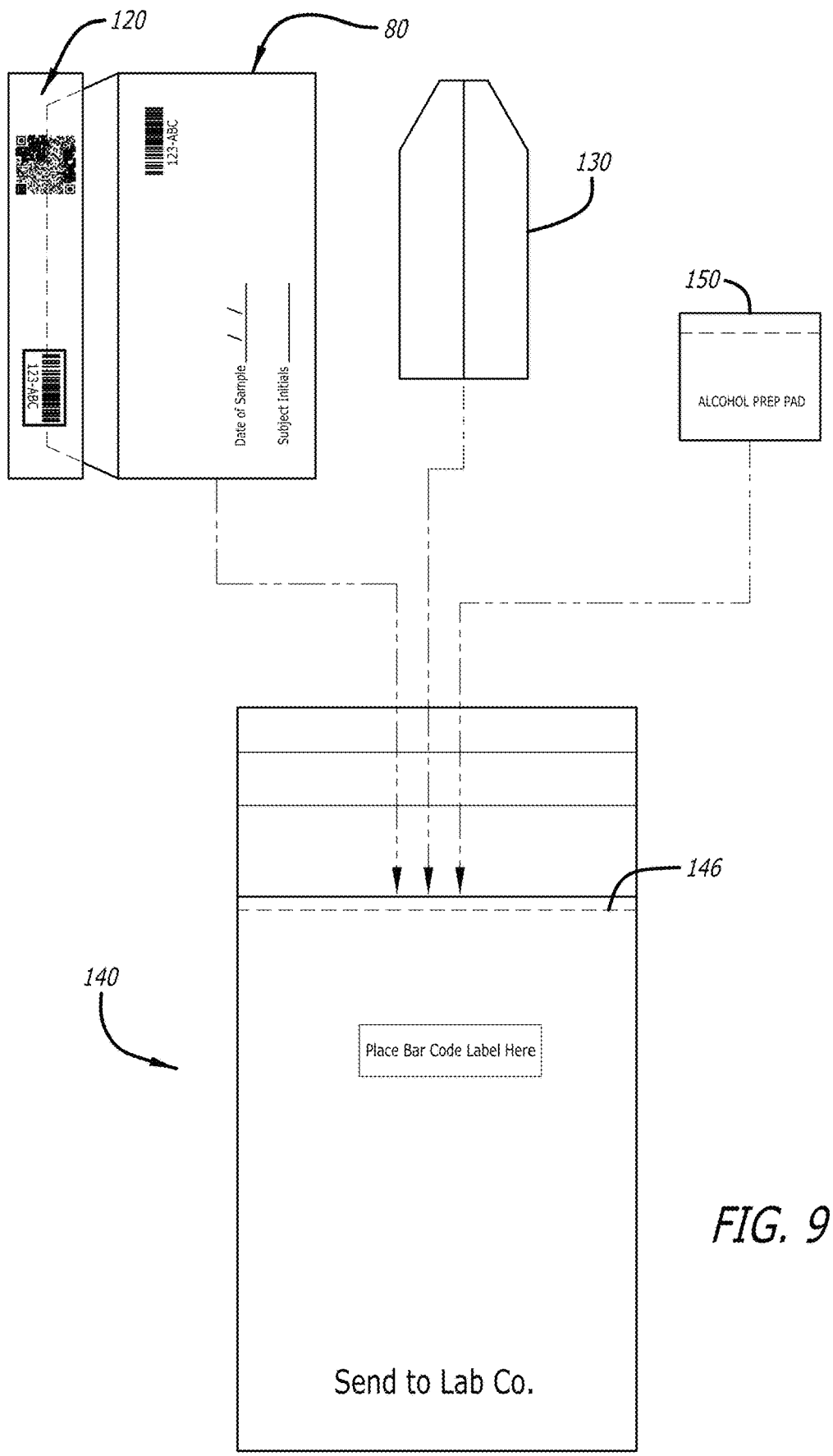
FIG. 9 shows an exemplary embodiment of a collection kit 100 disclosed herein.

In another embodiment, collection kit disclosed herein is assembled so that a collecting pouch serves as a container for the remaining components of the kit. A collecting pouch disclosed herein is secured in a manner to prevent the other components from falling out or being removed until needed, such as by employing the flap of a collecting pouch. In an aspect of this embodiment, and referring to FIG. 9, collection kit 100 comprises collecting pouch 140 which serves as a container and one or more identification labels 120, one or more sample containers 130, and sample shipping container 80. In another aspect of this embodiment, a collection kit 100 comprises collecting pouch 140 which serves as a container and one or more identification labels 120, one or more sample containers 130, sample shipping container 80, and instructions. In yet another aspect of this embodiment, a collection kit 100 comprises collecting pouch 140 which serves as a container and one or more identification labels 120, one or more sample containers 130, sample shipping container 80, and cleaning wipe 150. In still another aspect of this embodiment, a collection kit 100 comprises collecting pouch 140 which serves as a container and one or more identification labels 120, one or more sample containers 130, sample shipping container 80, cleaning wipe 150, and instructions. In some embodiments, collecting pouch 140 is secured in a manner to prevent the other components from falling out or being removed until needed, such as by an adhesive, a perforated seal that can be pulled off to enable access to the contents within or a zip-lock seal. For example, FIG. 9 shows a perforated top 146 is used to seal collecting pouch 140 in a manner that prevents the other components from falling out or being removed until needed.

Figure 2:
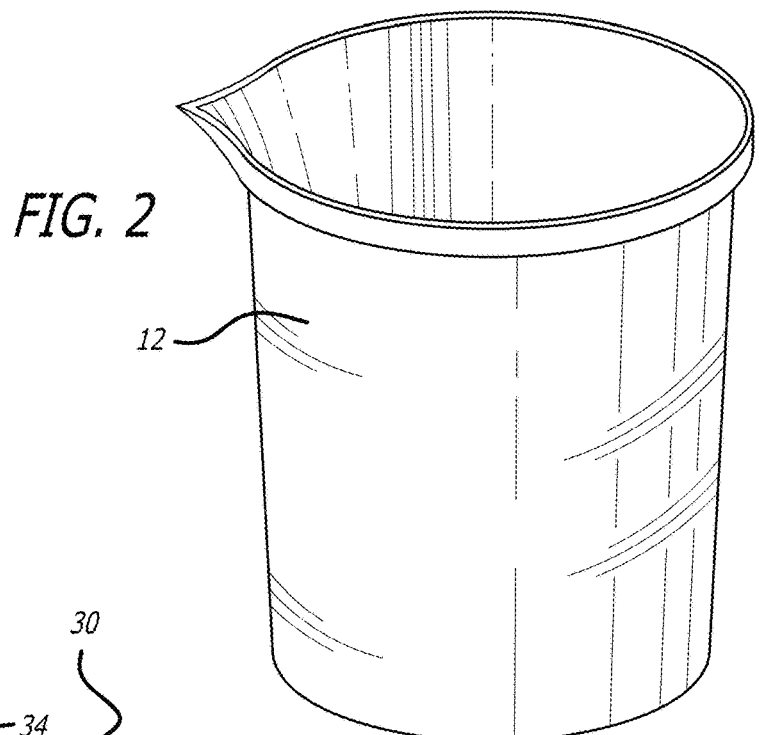
FIG. 2 shows a front perspective view of a sample collection device 12 disclosed herein.

Aspects of the present specification disclose a sample collection device. A sample collection device disclosed herein is used to collect a sample for subsequent evaluation from an individual, mechanical purpose, forensic site or anywhere a trackable container is useful or required. Although such a device can be used to transport the sample to a testing facility, a sample collection device is primarily used to collect a sample from an individual and then dispense an aliquot of the sample to the one or more sample containers. A sample collection device disclosed herein can be of any size and geometry but should be designed so that it is larger enough to collect an adequate amount of a sample from an individual for testing purposes and small enough to make manufacture, assembly, transportation, and storage convenient to the user. In an aspect of this embodiment, a sample collection device has a cylindrical cup-shaped design with a capacity to hold between 100 mL to 400 mL. In one embodiment, and referring to FIG. 2, a sample collection device 12 has a cylindrical cup-shaped design with a capacity to hold between 200 mL to 250 mL. Once a sample is dispensed to the one or more sample containers, a sample collection device, as well as any remaining sample can be disposed. As discussed above, a sample collection device disclosed herein can also function as an assembly container for the remaining components of a collection kit disclosed herein.

Aspects of the present specification disclose a sample shipping container. A sample shipping container is used to transport a sample container comprising a sample to a testing facility. A sample shipping container disclosed herein can be of any size and geometry but should be designed so that it is larger enough to receive one or more sample containers and small enough to make manufacture, assembly, transportation, and storage convenient to the user. A sample shipping container includes, without limitation, an envelope, canister mailing pouch, or a mailing box. In an aspect of this embodiment, and referring to FIG. 10A-B, a sample shipping container is an envelope 80 with front side 82 including sealing flap 86 and rear side 84.

Aspects of the present specification disclose a sample container. A sample container disclosed herein is used to save and seal for identification and tracking purposes a sample disclosed herein or aliquot thereof immediately after collection as well as during transportation, testing and storage. A sample container disclosed herein can be composed from any inert material suitable to store a sample disclosed herein, including without limitation a glass, metal or a plastic material. A sample container disclosed herein can be of any size and geometry but should be designed so that it is larger enough to contain an adequate amount of a collected sample from an individual for testing or further evaluation purposes and small enough to make manufacture, assembly, transportation, and storage convenient to the user. In an embodiment, a sample container disclosed herein should be of a size and geometry to fit the desired number of sample containers into a sample collection device disclosed herein during assembly. In aspects of this embodiment, a sample container may have a cylindrical shape and corresponding closure with a capacity to hold between 10 mL to 60 mL. In aspects of this embodiment, a sample container is a flat sheet of material having a width of 2 cm to 6 cm and a length of 9 cm to 14 cm.

Figure 3A:
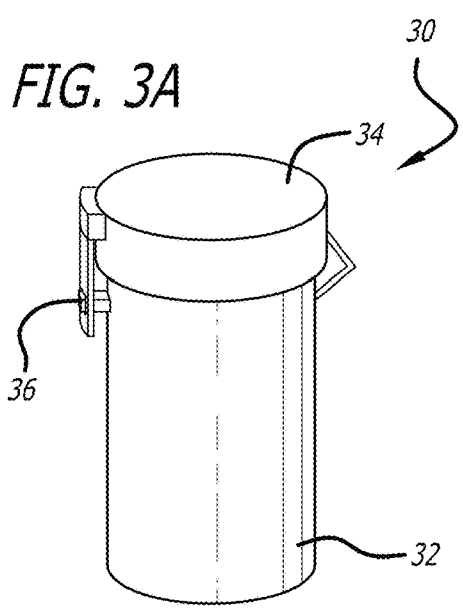
FIGS. 3A-B show an exemplary embodiment of a sample container 30 disclosed herein with FIG. 3A showing a front perspective view of sample container 30 with lid 34 closed.
Figure 3B:
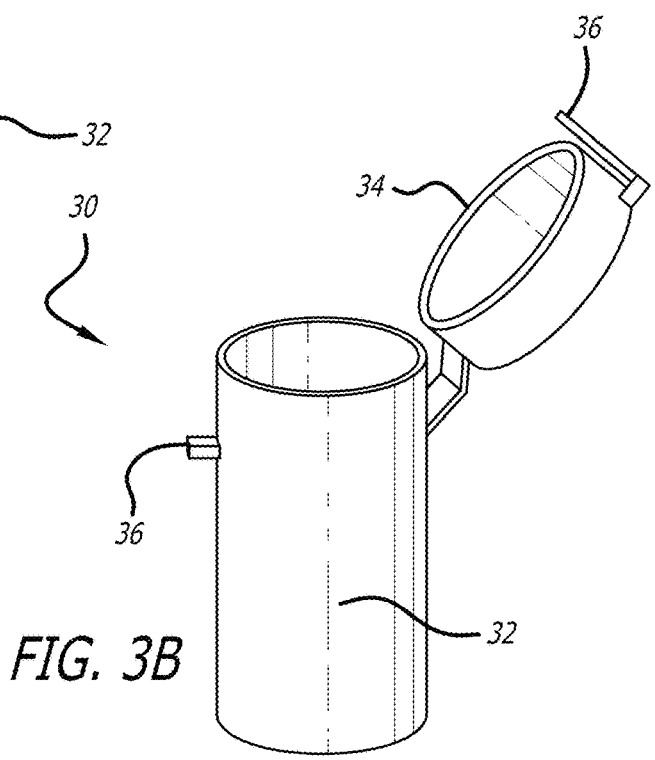

In one embodiment, and referring to FIGS. 3A-B, a sample container 30 comprises a container 32 and a lid 34. A container 32 disclosed herein is used to contain a sample or aliquot thereof. In an aspect of this embodiment, a sample contained in sample container 30 can be a liquid or a solid sample. A lid 34 disclosed here is used to seal the container in a manner that prevents sample leakage or contamination during, e.g., transportation and storage. For example, as illustrated in FIGS. 3A-B, sample container 30 can comprise a locking mechanism 36 that secures lid 34 to container 32 in a manner that prevents its opening unless locking mechanism 36 is released. In aspects of this embodiment, sample container 30 has a cylindrical design with a capacity to hold between 20 mL to 40 mL. In typical use, after a sample is collected in a sample collection device 12 disclosed herein, an aliquot of the sample is dispersed into a sample container 30 disclosed herein and then sealed with the lid 34.

A lid 34 can also be a tamper-proof design, thereby assuring that the sample container has been sealed since manufacture and thus unlikely to have been contaminated or adulterated. For example, as illustrated in FIGS. 7A-B, identification label 20 can be secured in a manner whereby in the process of opening lid 34 identification label 20 is torn or otherwise disfigured in a manner that indicates sample container 30 was opened.

Figure 11A:
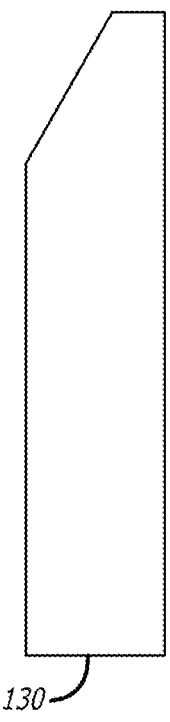
FIGS. 11A-B show an exemplary embodiment of a sample container 130 disclosed herein with FIG. 11A showing a side view of sample container 130.
Figure 11B:
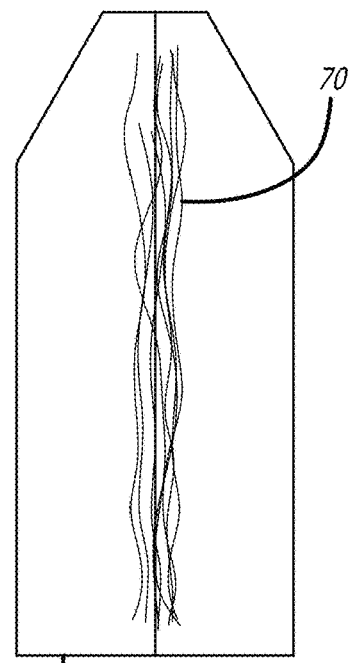

In another embodiment, and referring to FIG. 11A-B, a sample container 130 comprises a malleable or pliable, non-elastic material used to wrap or otherwise contain a sample, such as, e.g., a metal or plastic material. In another aspect of this embodiment, sample container 130 can be aluminum. In aspects of this embodiment, sample container 130 is a flat sheet of aluminum having a width of about 3 cm to 4 cm and a length of 10 cm to 11 cm. In another aspect of this embodiment, a sample 70 contained in sample container 130 can be a solid sample. In operation, a sample is place on one side of sample container 130, typically in a central location, and then sample container 130 is folded onto itself in a manner that wraps or otherwise contains a sample.

A sample container disclosed herein can be provided as a separate component or a component included in a collection kit disclosed herein. When provided as a separate component, an identification label will be associated with a sample container as an integrated component. For example, referring to FIG. 4E-G, identification label 20 is associated with lid 34.

The number of sample containers comprising a collection kit disclosed herein depends of the particular use and CoC requirements. Thus, in one embodiment, a kit disclosed herein comprises one sample container. In another embodiment, a collection kit disclosed herein comprises a plurality of sample containers. In yet another embodiment, a collection kit disclosed herein can comprise, e.g. one or more sample containers, two or more sample containers, three or more sample containers, four or more sample containers, or five or more sample containers. In still another embodiment, a collection kit disclosed herein can comprise, e.g. at most one sample container, at most two sample containers, at most three sample containers, at most four sample containers, or at most five sample containers. In still another embodiment, a collection kit disclosed herein can comprise, e.g. 1-2 sample containers, 1-3 sample containers, 1-4 sample containers, 1-5 sample containers, 2-3 sample containers, 2-4 sample containers, 2-5 sample containers, 3-4 sample containers, 3-5 sample containers, or 4-5 sample containers.

Figure 4A:
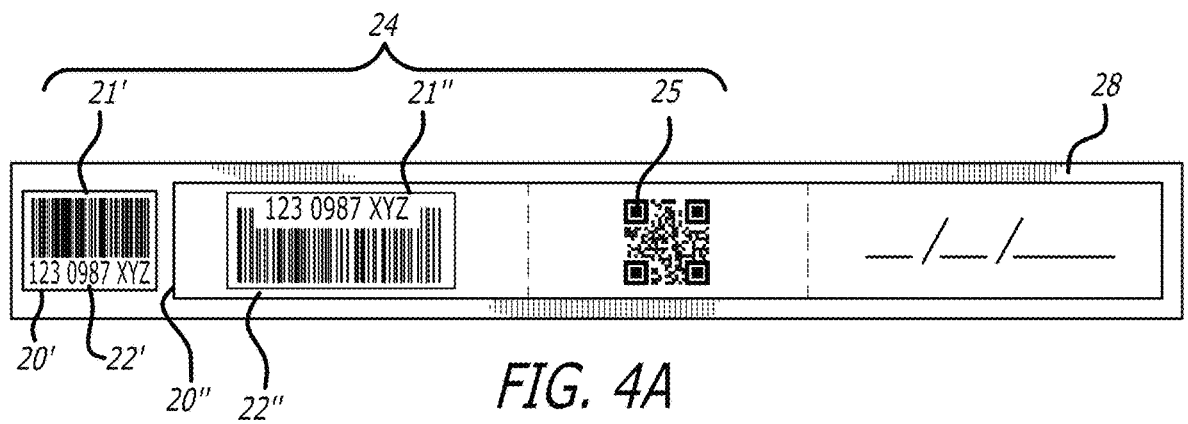
FIGS. 4A-G shows an exemplary embodiment of an identification label 20 disclosed herein with FIG. 4A showing top plan view of identification label 20 illustrating label side 22 with three different machine-readable codes 24.
Figure 4B:
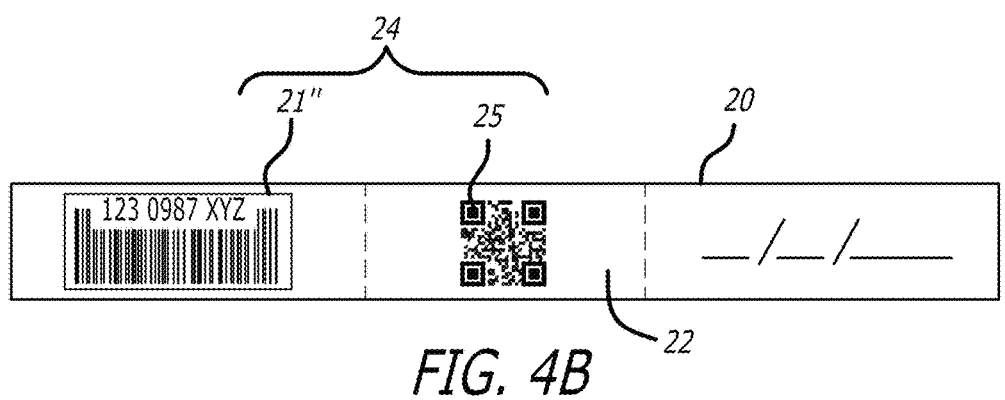
Figure 10A:
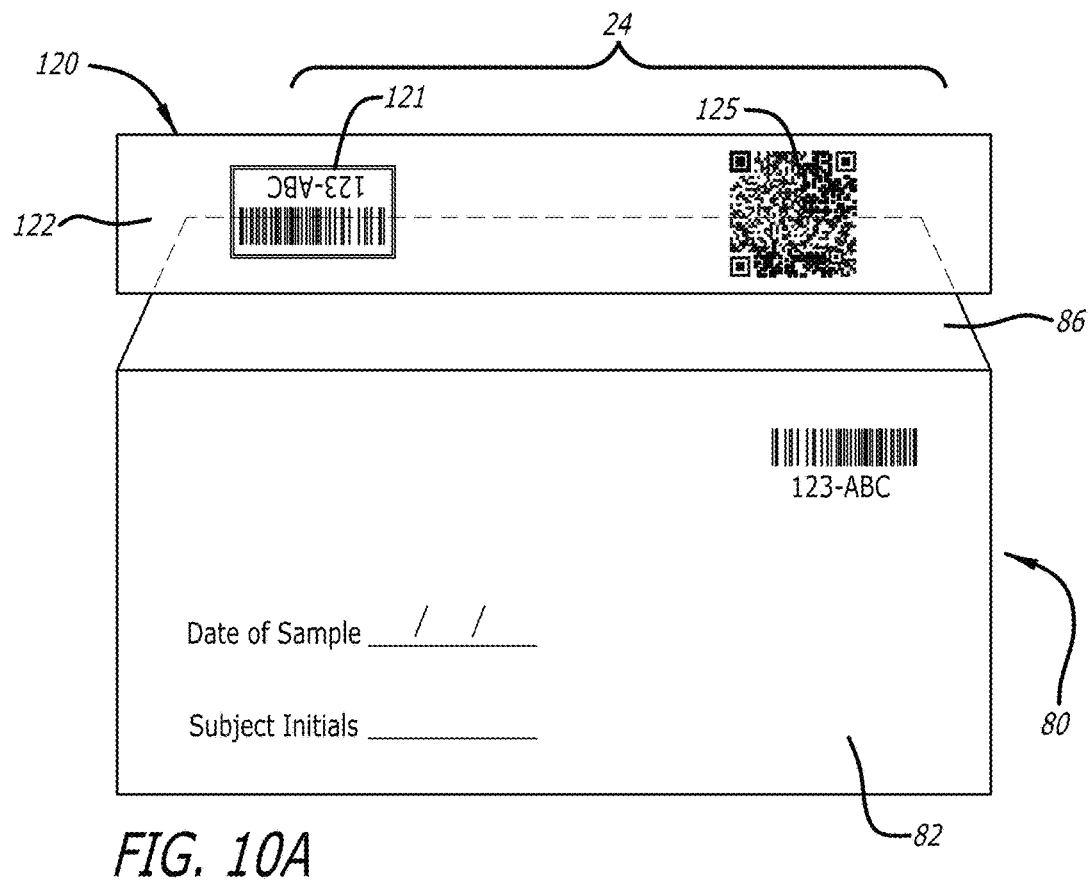
FIGS. 10A-B show an exemplary embodiment of a sample shipping container 80 disclosed herein with FIG. 10A showing view of front side elevational view of sample shipping container 80.
Figure 10B:
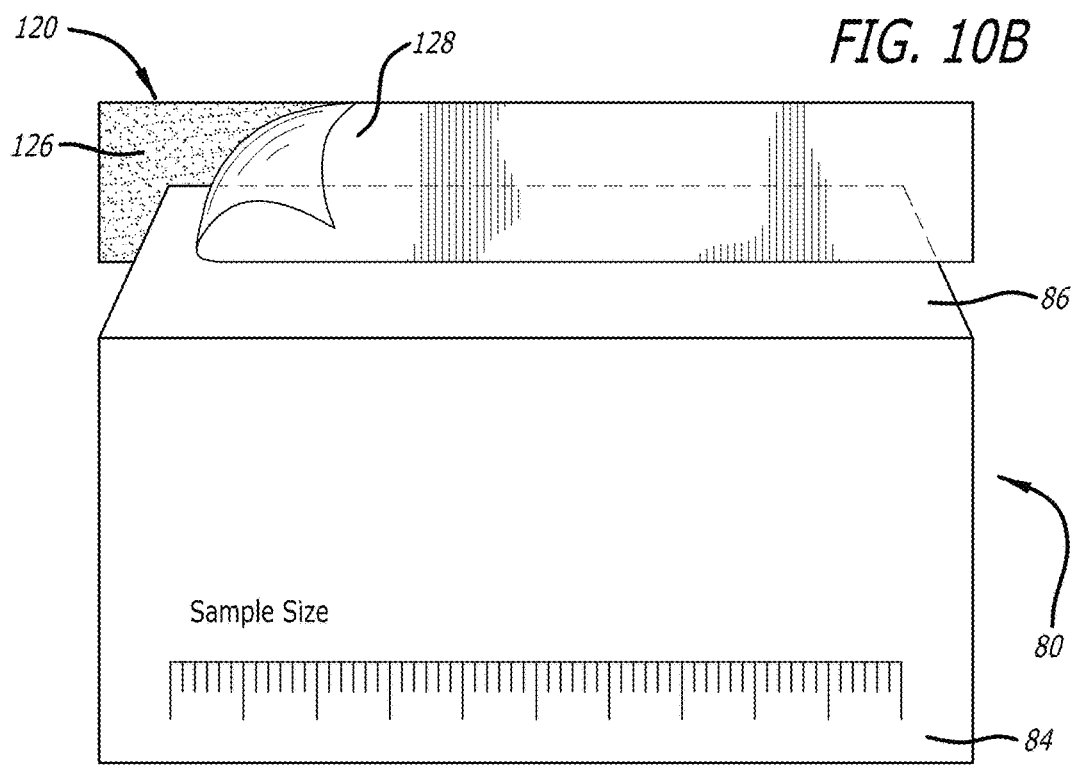

Aspects of the present specification disclose an identification label. An identification label disclosed herein is a medium capable of storing and displaying data in a format readable by a mechanical device. Referring to FIGS. 4A, 4B, & 4E, an identification label 20 disclosed herein comprises a label side 22 on one side having a machine-readable code 24 and an adhesive side 26 of the other side. Referring to FIGS. 10A-B, an identification label 120 disclosed herein comprises a label side 122 on one side having a machine-readable code 124 and an adhesive side 126 of the other side. A machine-readable code disclosed herein has unique identification characteristics. Non-limiting examples of machine-readable code 24, 124 include a bar code, a matrix code or two-dimensional bar code, a radio frequency identification (RFID), a magnetic strip, a microchip, and an optical character recognition (OCR).

In some embodiments, an identification label consists of a single identification label. In aspects of this embodiment, identification label can comprise a single machine-readable code. In other aspects of this embodiment, identification label can comprise more than one machine-readable codes. For example, as shown in FIG. 4B, identification label 20 consists of a single identification label 20 with label side 22 including two machine-readable codes 24, e.g., one bar code 21 and one OCR 25. As another example, as shown in FIG. 11A, identification label 120 consists of a single identification label 120 with label side 122 including two machine-readable codes 124, e.g., one bar code 121 and one OCR 125.

In some embodiments, identification label consists of more than one identification labels. In aspects of this embodiment, each of the more than one identification labels can comprise a single machine-readable code. In other aspects of this embodiment, each of the more than one identification labels can comprise more than one machine-readable codes. For example, as shown in FIG. 4A, identification label 20 consists of a first identification label 20' and second identification label 20". The first identification label 20' comprises a label side 22' including one machine-readable code 24, e.g., bar code 21' while the second identification label 20" comprises a label side 22" including more than one machine-readable codes 24, e.g., bar code 21" and OCR 25. In this arrangement, a first component can be affixed with first identification label 20 while a second component can be affixed with second identification label 20. For example, first identification label 20' comprising a label side 22' including one machine-readable code, e.g., bar code 21' can be affixed to collection pouch 40 from collection kit 10 while second identification label 20" comprising label side 22" including two machine-readable code, e.g., bar code 21" and OCR 25 can be affixed to sample container 30.

Typically an automatic identification and data capture (AIDC) method is employed to read the code in order to automatically identify the sample, collecting data about the sample, and enter the data directly into computer systems, without human involvement. An identification label disclosed 20 herein enables CoC procedures by tracking the one or more sample containers containing a sample throughout the entire process. The identification label tracks, for example, the chronological record of a sample, identifying information of the originating source of the sample, such as, e.g., the individual who donated the sample, the apparatus or location from where the sample was obtained, each person who collected and/or handled the sample, and the results obtained from analyzing the sample.

Figure 4C:
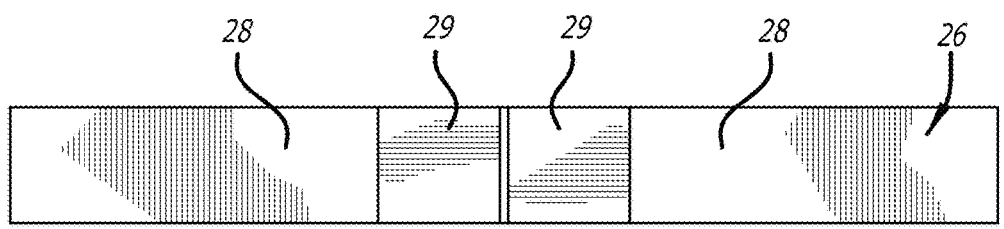
Figure 4D:
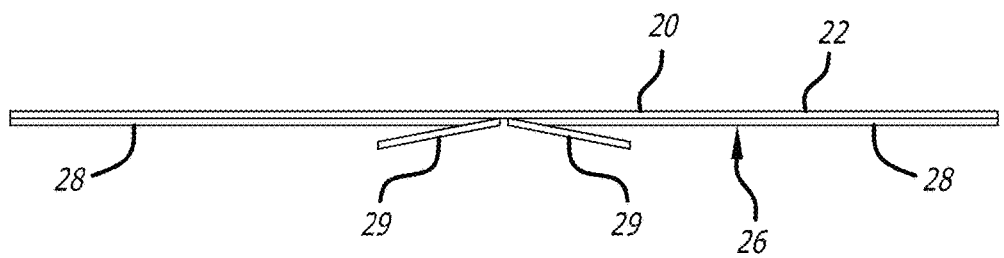
Figure 4E:
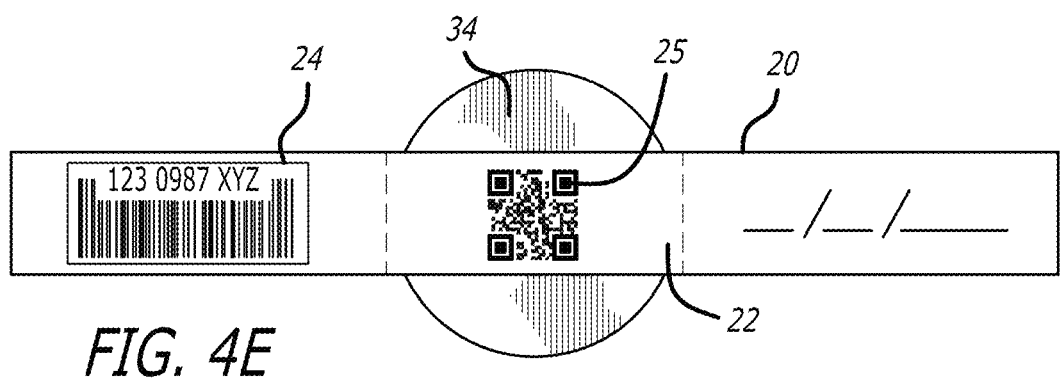
Figure 4F:
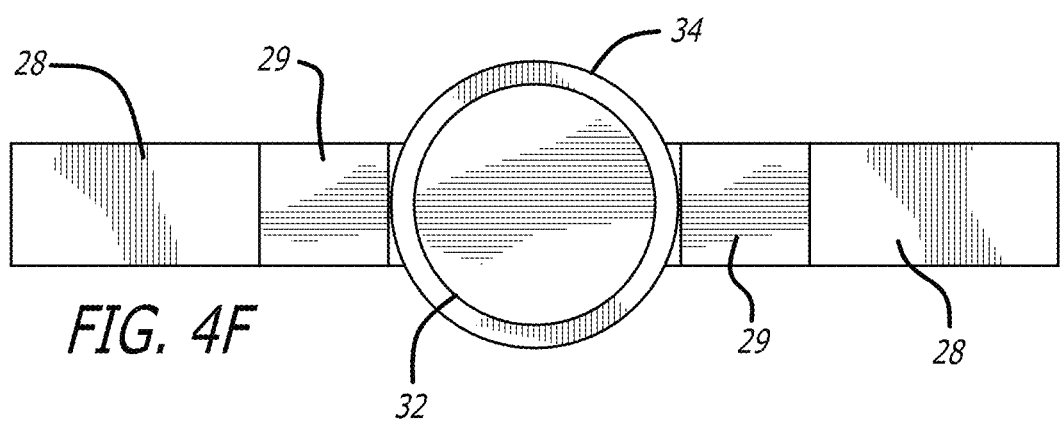
Figure 4G:
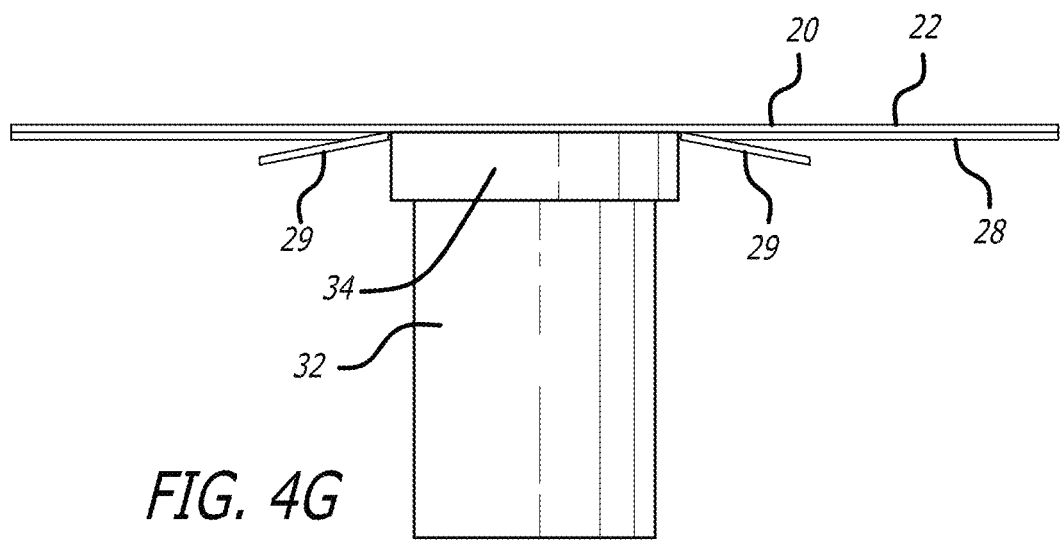

Referring to FIGS. 4A & 4C, adhesive side 26 of an identification label 20 comprises an adhesive (not shown) and a protective covering 28. An adhesive can cover all or a portion of adhesive side 26 and is used to affix identification label 20 to sample container 30. A protective covering 28 shields or otherwise prevents the adhesive from debris, inappropriate affixing or other events fouling or otherwise making the adhesive inoperable for its intended use. In some embodiments, and as best seen in FIG. 4A, protective covering 28 is a simple sheet. In some embodiments, and as best shown in FIGS. 4C, 4D & 4G protective covering 28 can comprise one or more tabs 29. As a user of a collection kit disclosed herein will in all likelihood be wearing protective gloves to the handling of a sample, tab 29 facilitates easy removal of protective covering 28 from adhesive side 26 of identification label 20 in order to expose an adhesive. Containers having an integrated identification label enable serialization of machine-readable codes in consecutive order that facilitate data reporting and tracking with respect to inventory usage. In an aspect of this embodiment, a collection kit disclosed herein contains a plurality of containers each having an integrated identification label serialization with machine-readable codes in consecutive order.

In one embodiment, an identification label can be a component separate from the other components including a sample container. For example, FIGS. 1 & 4A-D illustrate identification label 20 as a component separate from the other components including a sample container. Once a sample is aliquoted to container 32 of a sample container 30 disclosed herein it is sealed using lid 34. Identification label 20 is then affixed to the sample container by removing protective covering 28 on adhesive side 26 of identification label 20 to expose an adhesive. Identification label 20 is then secured to sample container 30 by placing identification label 20 adhesive side down across lid 34 and down at least one side of container 32 (FIG. 7).

In another embodiment, an identification label is associated with a sample container as an integrated component. In aspects of this embodiment, an identification label is associated with a lid of a sample container. For example, referring to FIG. 4E-G, identification label 20 is associated with lid 34 and identification label 20 has one or more portions that remain unassociated with lid 34. Adhesive side 26 of the one or more unassociated portions of identification label 20 are covered with protective covering 28 that can optionally comprise one or more tabs 29. Once a sample is aliquoted to container 32 of sample container 30 disclosed herein it is sealed using lid 34. Protective covering 28 is removed from the one or more unassociated portions of identification label 20 to expose adhesive side 26. The one or more unassociated portions of identification label 20 are then affixed to the sides of a sample container. One or more sides of identification label 20 comprising adhesive is then secured to sample container 30 by placing the one or more sides of identification label 20 down at least one side of container 32.

In one embodiment, an identification label can be a component separate from the other components including a sample shipping container. In another embodiment, an identification label is associated with a sample shipping container as an integrated component. For example, referring to FIG. 10A-B, identification label 120 comprising label side 122 and adhesive side 126 including adhesive (not shown) and protective covering 128 is associated with or comprises sealing flap 86 of sample shipping container 80. Once sample container 130 comprising a sample is placed in sample shipping container 80, protective covering 128 from adhesive side 126 of identification label 120 to expose an adhesive. Sealing flap 86 comprising identification label 120 is then affixed to the sample shipping container by securing exposed adhesive to rear side 84 of sample shipping container 80.

Generally, the number of identification labels disclosed herein is equal to the number of sample container provided in a collection kit. Thus, in one embodiment, a collection kit disclosed herein that comprises one sample container will include one identification label. In another embodiment, a collection kit disclosed herein that comprises a plurality of sample containers will include the same number of identification labels as the plurality of sample containers. In yet another embodiment, a collection kit disclosed herein that comprises, e.g. two sample containers will contain two identification labels, three sample containers will contain three identification labels, four sample containers will contain four identification labels, or five sample containers will contain five identification labels.

An identification label disclosed herein as it pertains to a collection kit disclosed herein has several advantages over current CoC procedures. For example, by providing an identification label a collection kit disclosed herein dispenses with the need of hard-copy CoC forms. In addition, an identification label disclosed herein is compatible with all software systems used to initiate a COC procedure and dispenses with the need to print out a tracking label. Furthermore, an identification label disclosed herein facilitates tracking of document failures, such as, e.g., incorrect or incomplete collection, handling or processing irregularities, thereby ensuring compliance with required or otherwise specified CoC procedures determined by a governing authority.

Aspects of the present specification disclose a sample, e.g., sample 70 of FIGS. 7, 8, & 11B. A sample can be a biological sample or a non-biological sample. A sample can be a non-hazardous material or a hazardous material such as, e.g., an infectious, a toxic, a radioactive or other biohazardous material. Non-limiting examples of a biological sample include urine, fecal matter, hair, blood, saliva, skin/epidermal cells, muscle, an internal organ, a pathogen, a plant or material derived or collected from a plant, or foodstuff. Non-limiting examples of a non-biological sample include dirt, debris from an explosion or accident, rocks, glass, water, oil, gas or other petroleum product, a fossil or any other non-biological material that can be procured off of an individual, apparatus or location and collected as a sample disclosed herein.

A sample disclosed herein can be a sample obtained from an individual, an apparatus, or a location. An individual can be a human or an animal. An animal includes, without limitation, a mammal, a bird, a reptile, an amphibian, or a fish. An apparatus includes, without limitation, a machine or device. A location can be a discriminate or indiscriminate indoor location, such as, e.g., inside a container, vehicle, building, or a discriminate or indiscriminate outdoor location, such as, e.g., a street, park, forest, desert, ocean, sea, river or other waterway.

Figure 5:
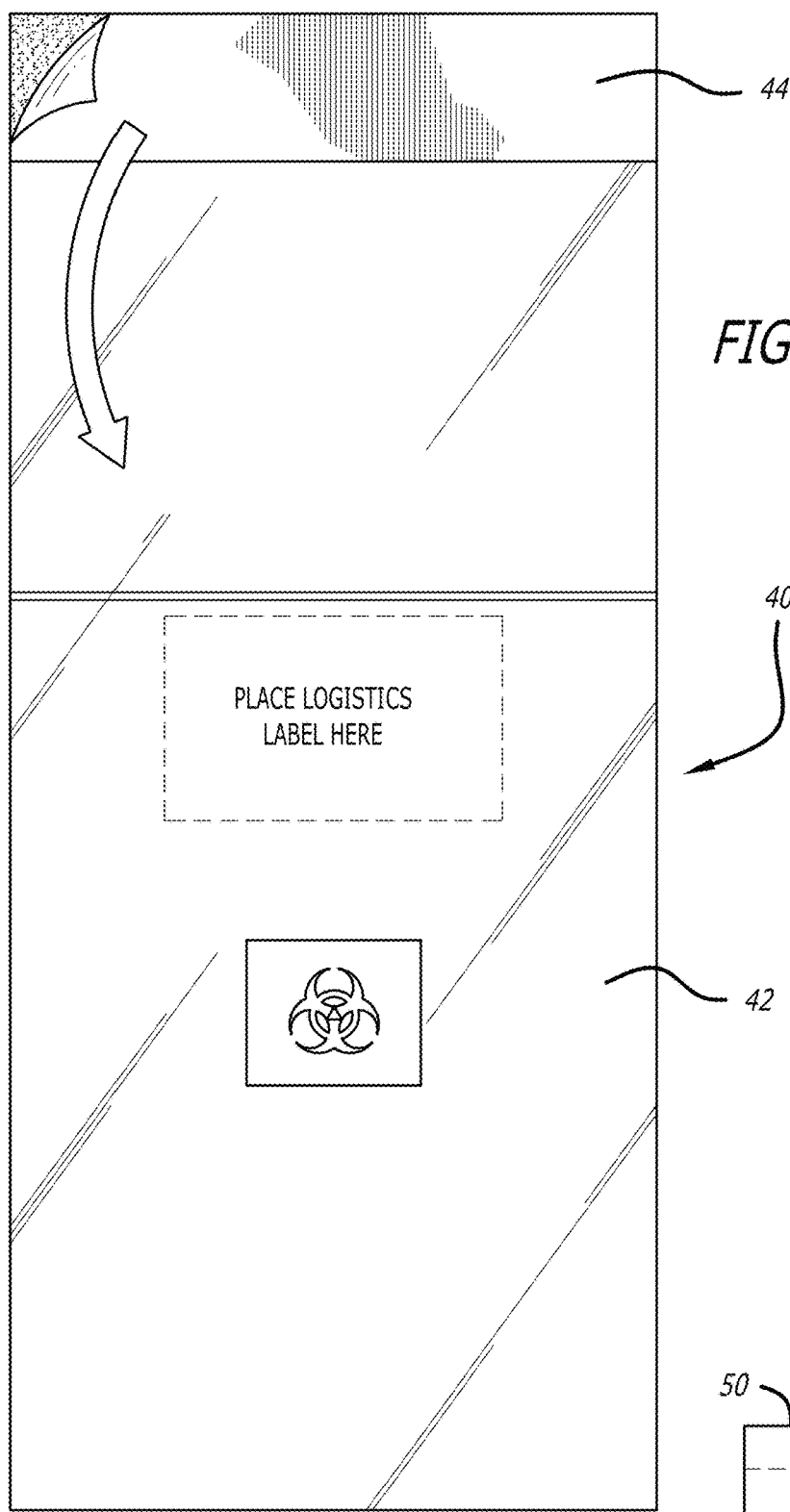
FIG. 5 shows an exemplary embodiment of a collecting pouch 40 disclosed herein.
Figure 12:
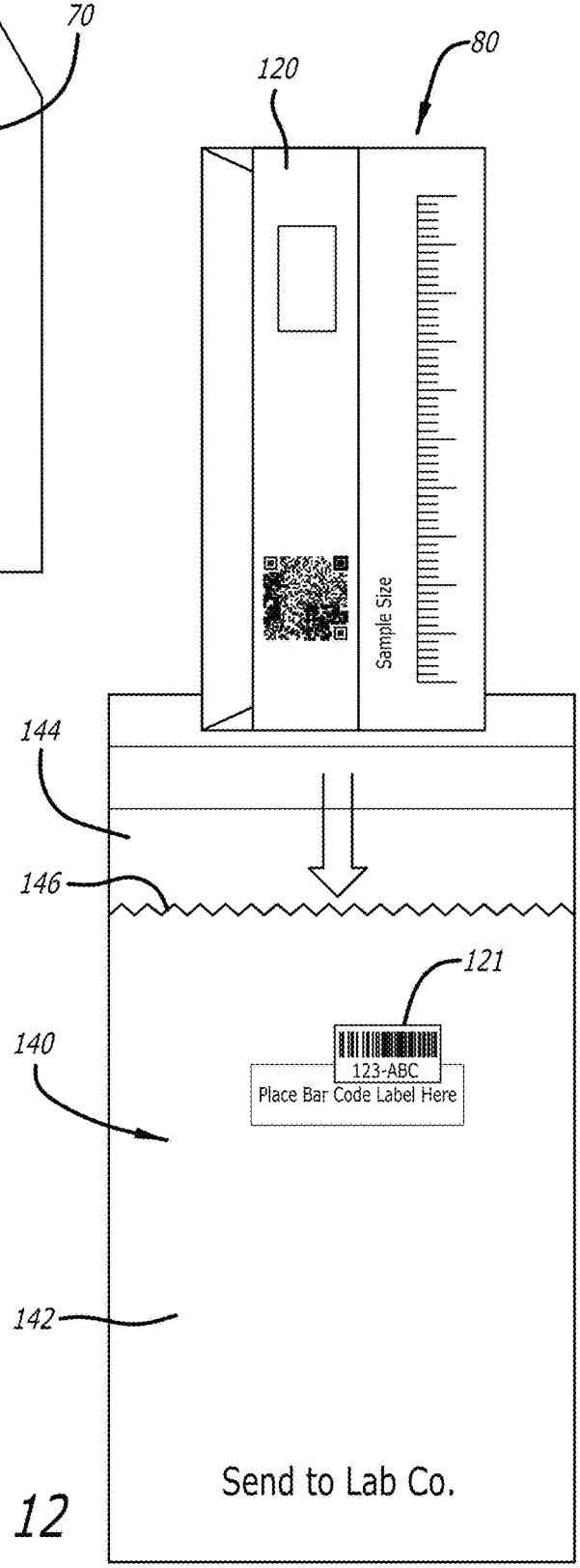
FIG. 12 shows an exemplary embodiment of a collecting pouch 140 disclosed herein.

Aspects of the present specification disclose a collecting pouch. Referring to FIGS. 5 & 11, a collecting pouch 40 or 140 disclosed herein is used to secure the one or more sample containers 30 or sample shipping container 80 comprising sample 70 for transportation. As a collected sample could be considered a bio-hazard, a collecting pouch disclosed herein helps prevent contamination of sample 70 from the collection site to the testing facility as well as prevents contamination due to spillage sample 70. Thus, a collecting pouch disclosed herein is designed in a manner that it can be sealed once the one or more sample contained are placed inside the pouch (FIG. 8). For example, a collecting pouch can comprise a flap with an adhesive or an interlocking groove and ridge that forms a tight seal when pressed together, thereby closing the pouch opening. In one embodiment, and referring to FIG. 5, a collecting pouch 40 disclosed herein comprises a pouch 42 and a flap 44. In another embodiment, and referring to FIG. 12, a collecting pouch 140 disclosed herein comprises a pouch 142 and a flap 144. Collecting pouch 40, 140, can also optionally include a designated spot to affix identification label 20 as well as optionally including a designated spot to indicate testing facility address and/or biohazard markings.

Aspects of the present specification disclose instructions. Instructions disclosed herein provide information to the individual who is donating a biological sample and/or a collector who is monitoring and/or sending the collected samples to a testing facility. In one embodiment, step-by-step instructions pertaining to the use of the components comprising kit for the collection of a biological sample. For example, information can include instructions to a donor in how to provide a biological sample for testing, such as, e.g., how to check the integrity of a collection kit and the components therein, how to prevent contamination of a biological sample during collection, how to prepare his/her person for obtaining a biological sample, how to collect a biological sample using a sample collection device, and how to aliquot a biological sample to one or more sample containers. Information can include instructions to a collector in how to administer the collection and transportation of a biological sample from a donor, such as, e.g., how to check the integrity of a collection kit and the components therein, how to prevent contamination of a biological sample during collection, how to observe the donor for proper collection of a biological sample, how to affix the identification labels to each sample container, how to package the sample containers in collecting pouch, and how to package a biological sample for transportation to a testing facility. Instructions disclosed herein can be provided together or separately, e.g., an instruction sheet for a donor and a separate instruction sheet for a collector. In addition, instructions can be separated based on gender. i.e., separate instructions for a male donor and a female donor.

Figure 6:
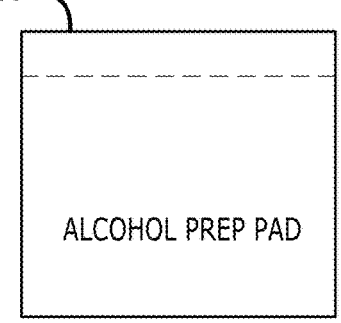
FIG. 6 shows an exemplary embodiment of a cleaning wipe 50 disclosed herein.
Figure 13:
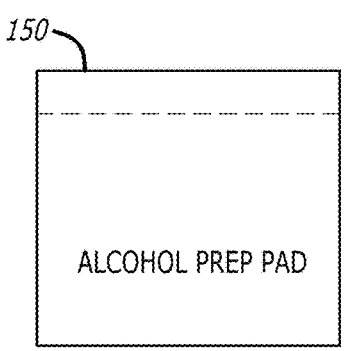
FIG. 13 shows an exemplary embodiment of a cleaning wipe 150 disclosed herein.

Aspects of the present specification disclose a cleaning wipe. A cleaning wipe disclosed herein is used to prepare the person of a donor to ensure proper collection of a biological sample that maintains its integrity and avoids contamination. Non-limiting examples of a cleaning wipe include a cloth material, a cotton ball or a paper towel and of which can be presoaked with an alcohol, such as ethanol or isopropanol. In an aspect of this embodiment, and referring to FIG. 6, cleaning wipe 50 is a cloth material. A cleaning wipe can be in its own container to keep it sanitary and can be saturated with a cleaning or disinfectant solution, such as an alcohol. In an aspect of this embodiment, and referring to FIG. 13, cleaning wipe 150 is an alcohol wipe sealed in a pouch.

The present specification also discloses methods and uses for collecting a biological sample using a collection kit disclosed herein. In one embodiment, methods and uses disclosed herein are for collecting a biological sample from a human. In another embodiment, methods and uses disclosed herein are for collecting a biological sample from an animal.

In one embodiment, a method comprises collecting a biological sample from an individual using a collection kit disclosed herein. In aspects of this embodiment, a method comprises collecting a biological sample from an individual using a collection kit disclosed herein and affixing an identification label provided by the kit to each of the one or more sample containers comprising a sample. In other aspects of this embodiment, a method comprises collecting a biological sample from an individual using a collection kit disclosed herein, affixing an identification label provided by the kit to each of the one or more sample containers comprising a sample and associating information on the originating source or the sample and/or testing instructions with the identification label. In yet other aspects of this embodiment, a method comprises collecting a biological sample from an individual using a collection kit disclosed herein, affixing an identification label provided by the kit to each of the one or more sample containers comprising a sample, associating information on the originating source or the sample and/or testing instructions with the identification label, and transporting the collected biological sample to a testing facility for analysis.

In one embodiment, a collection kit disclosed herein is used for collecting a biological sample from an individual. In aspects of this embodiment, a collection kit disclosed herein is used for collecting a biological sample from an individual and affixing an identification label provided by the kit to each of the one or more sample containers comprising a sample. In other aspects of this embodiment, a collection kit disclosed herein is used for collecting a biological sample from an individual, affixing an identification label provided by the kit to each of the one or more sample containers comprising a sample and associating information on the originating source or the sample and/or testing instructions with the identification label. In yet other aspects of this embodiment, a collection kit disclosed herein is used for collecting a sample from an individual, affixing an identification label provided by the kit to each of the one or more sample containers comprising a sample, associating information on the originating source or the sample and/or testing instructions with the identification label, and transporting the collected biological sample to a testing facility for analysis.

A collection kit or sample container disclosed herein can for medical or veterinary purposes. A medical or veterinary purpose includes drug testing, genotype testing, disease testing, or biomarker testing. A collection kit or sample container disclosed herein can also be used for criminal, forensic or archaeological purposes or any other purpose where accurate CoC procedures are required or desired. A collection kit or sample container disclosed herein can also be used for universal purposes such as analysis of material or chemical make-up related to molecular composition or properties such as toxicology, viscosity, hysteresis and other related findings.

Aspects of the present specification can also be described as follows:

1. A kit for collecting a biological sample, the kit comprising a sample collection device and one or more other components, wherein the one or more other components comprise one or more identification labels, wherein the one or more identification labels each comprise one or more machine-readable codes with unique identification characteristics on one side and an adhesive on the other side.
2. The kit according to embodiment 1, wherein the sample collection device serves as a container for the one or more other components.
3. The kit according to embodiment 1 or 2, wherein the sample collection device has a cylindrical cup-shaped design with a capacity to hold between 100 mL to 400 mL.
4. The kit according to embodiment 3, wherein the sample collection device has a cylindrical cup-shaped design with a capacity to hold between 200 mL to 250 mL.
5. The kit according to any one of embodiments 1-4, wherein the machine-readable code comprises a bar code, a matrix code or two-dimensional bar code, a radio frequency identification (RFID), a magnetic strip, a microchip, or an optical character recognition (OCR).
6. The kit according to any one of embodiments 1-5, wherein the one or more other components comprise one or more sample containers, the one or more sample containers each comprising a container and a lid.
7. The kit according to embodiment 6, wherein each of the one or more identification labels is integrated onto the lid.
8. The kit according to embodiment 6, wherein the one or more sample containers each have a cylindrical cup-shaped design with a capacity to hold between 20 mL to 40 mL.
9. The kit according to embodiment 6, wherein the kit comprises one to five sample containers.
10. The kit according to any one of embodiments 1-9, wherein the one or more other components comprise a collecting pouch.
11. The kit according to any one of embodiments 1-10, wherein the one or more other components comprise instructions.
12. The kit according to embodiment 11, wherein the instructions pertain to the use of the components comprising kit for the collection of a biological sample and/or pertain to the collection and transportation of a biological sample obtained from a donor.
13. The kit according to any one of embodiments 1-12, wherein the one or more other components comprise a cleaning wipe.
14. The kit according to any one of embodiments 1-13, wherein the sample is collected from an individual, an apparatus, a location, or any combination thereof.
15. The kit according to any one of embodiments 1-14, wherein the sample is a biological sample, a non-biological sample, or both.

16. A method of collecting a sample, the method comprising collecting a sample using a kit comprising a sample collection device, one or more identification labels, each identification label comprising one or more machine-readable codes with unique identification characteristics, one or more sample containers, a collecting pouch, instructions and a cleaning wipe, wherein the sample is collected using the sample collection device.

17. The method according to embodiment 16, wherein the method further comprises affixing an identification label from the one or more identification labels to each of the one or more sample containers comprising a sample.

18. The method according to embodiment 17, wherein the method further comprises associating information on the originating source or the sample and/or testing instructions with the machine-readable code contained on the one or more identification labels.

19. The method according to embodiment 18, wherein the method further comprises transporting the collected sample to a facility for subsequent testing or analysis.

20. The method according to any one of embodiments 16-19, wherein the sample is obtained from urine, hair, blood, saliva or skin/epidermal cells.

21. The method according to any one of embodiments 16-20, used for a medical purpose, a veterinary purpose, a criminal investigatory purpose, a forensic purpose, an environmental evaluation purpose, or an archaeological purpose 22. A kit for use in collecting a sample from an individual, wherein the kit comprising a sample collection device, one or more identification labels, each identification label comprising a machine-readable code with unique identification characteristics, one or more sample containers, a collecting pouch, instructions and a cleaning wipe, wherein the sample is collected using the sample collection device.

23. A kit for collecting a sample, the kit comprising a collecting pouch and one or more other components, wherein the one or more other components comprise a sample shipping container, the sample shipping container being a mailing envelope with a sealing flap; and one or more identification labels, the one or more identification labels each comprising a machine-readable code with unique identification characteristics on one side and an adhesive on the other side.

24. The kit according to embodiment 23, wherein the collecting pouch serves as a container for the one or more other components.

25. The kit according to embodiment 23 or 24, wherein the machine-readable code comprises a bar code, a matrix code or two-dimensional bar code, a radio frequency identification (RFID), a magnetic strip, a microchip, or an optical character recognition (OCR).

26. The kit according to any one of embodiments 23-25, wherein the one or more sample containers is a flat sheet of aluminum.

27. The kit according to any one of embodiments 23-26, wherein each of the one or more identification labels is integrated onto the sealing flap.

28. The kit according to any one of embodiments 23-27, wherein the one or more other components comprise instructions.

29. The kit according to embodiment 28, wherein the instructions pertain to the use of the components comprising kit for the collection of a sample and/or pertain to the collection and transportation of a sample obtained from a donor or objects or materials at collection site.

30. The kit according to any one of embodiments 23-29, wherein the one or more other components comprise a cleaning wipe.

31. The kit according to any one of embodiments 23-30, wherein the sample is collected from an individual, an apparatus, a location, or any combination thereof.

32. The kit according to claim 23, wherein the sample is a biological sample, a non-biological sample, or both.

33. A sample container comprising a container, a lid and an identification labels, the identification label comprising one or more machine-readable codes with unique identification characteristics on one side and an adhesive on the other side, wherein the identification label has a portion affixed to the lid and one or more portions unassociated with the sample container, the side having the adhesive of one or more unassociated portions being covered by a protective covering, the protective covering optionally comprising a tab.

34. The sample container according to embodiment 33, wherein the machine-readable code comprises a bar code, a matrix code or two-dimensional bar code, a radio frequency identification (RFID), a magnetic strip, a microchip, or an optical character recognition (OCR).

35. The sample container according to embodiment 33 or 34, wherein the sample container has a cylindrical cup-shaped design with a capacity to hold between 20 mL to 40 mL.

In closing, it is to be understood that although aspects of the present specification are highlighted by referring to specific embodiments, one skilled in the art will readily appreciate that these disclosed embodiments are only illustrative of the principles of the subject matter disclosed herein. Therefore, it should be understood that the disclosed subject matter is in no way limited to a particular compound, composition, article, apparatus, methodology, protocol, and/or reagent, etc., described herein, unless expressly stated as such. In addition, those of ordinary skill in the art will recognize that certain changes, modifications, permutations, alterations, additions, subtractions and sub-combinations thereof can be made in accordance with the teachings herein without departing from the spirit of the present specification. It is therefore intended that the following appended claims and claims hereafter introduced are interpreted to include all such changes, modifications, permutations, alterations, additions, subtractions and sub-combinations as are within their true spirit and scope.

Certain embodiments of the present invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the present invention to be practiced otherwise than specifically described herein. Accordingly, this invention includes all modifications and equivalents of the subject matter recited in the claims appended hereto as permitted by applicable law. Moreover, any combination of the above-described embodiments in all possible variations thereof is encompassed by the invention unless otherwise indicated herein or otherwise clearly contradicted by context.

Groupings of alternative embodiments, elements, or steps of the present invention are not to be construed as limitations. Each group member may be referred to and claimed individually or in any combination with other group members disclosed herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Unless otherwise indicated, all numbers expressing a characteristic, item, quantity, parameter, property, term, and so forth used in the present specification and claims are to be understood as being modified in all instances by the term "about." As used herein, the term "about" means that the characteristic, item, quantity, parameter, property, or term so qualified encompasses a range of plus or minus ten percent above and below the value of the stated characteristic, item, quantity, parameter, property, or term. Accordingly, unless indicated to the contrary, the numerical parameters set forth in the specification and attached claims are approximations that may vary. For instance, as mass spectrometry instruments can vary slightly in determining the mass of a given analyte, the term "about" in the context of the mass of an ion or the mass/charge ratio of an ion refers to +/−0.50 atomic mass unit. At the very least, and not as an attempt to limit the application of the doctrine of equivalents to the scope of the claims, each numerical indication should at least be construed in light of the number of reported significant digits and by applying ordinary rounding techniques.

Use of the terms "may" or "can" in reference to an embodiment or aspect of an embodiment also carries with it the alternative meaning of "may not" or "cannot." As such, if the present specification discloses that an embodiment or an aspect of an embodiment may be or can be included as part of the inventive subject matter, then the negative limitation or exclusionary proviso is also explicitly meant, meaning that an embodiment or an aspect of an embodiment may not be or cannot be included as part of the inventive subject matter. In a similar manner, use of the term "optionally" in reference to an embodiment or aspect of an embodiment means that such embodiment or aspect of the embodiment may be included as part of the inventive subject matter or may not be included as part of the inventive subject matter. Whether such a negative limitation or exclusionary proviso applies will be based on whether the negative limitation or exclusionary proviso is recited in the claimed subject matter.

Notwithstanding that the numerical ranges and values setting forth the broad scope of the invention are approximations, the numerical ranges and values set forth in the specific examples are reported as precisely as possible. Any numerical range or value, however, inherently contains certain errors necessarily resulting from the standard deviation found in their respective testing measurements. Recitation of numerical ranges of values herein is merely intended to serve as a shorthand method of referring individually to each separate numerical value falling within the range. Unless otherwise indicated herein, each individual value of a numerical range is incorporated into the present specification as if it were individually recited herein.

The terms "a," "an," "the" and similar references used in the context of describing the present invention (especially in the context of the following claims) are to be construed to cover both the singular and the plural, unless otherwise indicated herein or clearly contradicted by context. Further, ordinal indicators—such as "first," "second," "third," etc.— for identified elements are used to distinguish between the elements, and do not indicate or imply a required or limited number of such elements, and do not indicate a particular position or order of such elements unless otherwise specifically stated. All methods described herein can be performed in any suitable order unless otherwise indicated herein or otherwise clearly contradicted by context. The use of any and all examples, or exemplary language (e.g., "such as") provided herein is intended merely to better illuminate the present invention and does not pose a limitation on the scope of the invention otherwise claimed. No language in the present specification should be construed as indicating any non-claimed element essential to the practice of the invention.

When used in the claims, whether as filed or added per amendment, the open-ended transitional term "comprising", variations thereof such as "comprise" and "comprises", and equivalent open-ended transitional phrases thereof like "including," "containing" and "having", encompasses all the expressly recited elements, limitations, steps, integers, and/or features alone or in combination with unrecited subject matter; the named elements, limitations, steps, integers, and/or features are essential, but other unnamed elements, limitations, steps, integers, and/or features may be added and still form a construct within the scope of the claim. Specific embodiments disclosed herein may be further limited in the claims using the closed-ended transitional phrases "consisting of" or "consisting essentially of" (or variations thereof such as "consist of", "consists of", "consist essentially of", and "consists essentially of") in lieu of or as an amendment for "comprising." When used in the claims, whether as filed or added per amendment, the closed-ended transitional phrase "consisting of" excludes any element, limitation, step, integer, or feature not expressly recited in the claims. The closed-ended transitional phrase "consisting essentially of" limits the scope of a claim to the expressly recited elements, limitations, steps, integers, and/or features and any other elements, limitations, steps, integers, and/or features that do not materially affect the basic and novel characteristic(s) of the claimed subject matter. Thus, the meaning of the open-ended transitional phrase "comprising" is being defined as encompassing all the specifically recited elements, limitations, steps and/or features as well as any optional, additional unspecified ones. The meaning of the closed-ended transitional phrase "consisting of" is being defined as only including those elements, limitations, steps, integers, and/or features specifically recited in the claim whereas the meaning of the closed-ended transitional phrase "consisting essentially of" is being defined as only including those elements, limitations, steps, integers, and/or features specifically recited in the claim and those elements, limitations, steps, integers, and/or features that do not materially affect the basic and novel characteristic(s) of the claimed subject matter. Therefore, the open-ended transitional phrase "comprising" (and equivalent open-ended transitional phrases thereof) includes within its meaning, as a limiting case, claimed subject matter specified by the closed-ended transitional phrases "consisting of" or "consisting essentially of." As such embodiments described herein or so claimed with the phrase "comprising" are expressly or inherently unambiguously described, enabled and supported herein for the phrases "consisting essentially of" and "consisting of."

All patents, patent publications, and other references cited and identified in the present specification are individually and expressly incorporated herein by reference in their entirety for the purpose of describing and disclosing, for example, the compositions and methodologies described in such publications that might be used in connection with the present invention. These publications are provided solely for their disclosure prior to the filing date of the present application. Nothing in this regard is or should be construed as an admission that the inventors are not entitled to antedate such disclosure by virtue of prior invention or for any other reason. All statements as to the date or representation as to the contents of these documents is based on the information available to the applicant and does not constitute any admission as to the correctness of the dates or contents of these documents.

Lastly, the terminology used herein is for the purpose of describing particular embodiments only and is not intended to limit the scope of the present invention, which is defined solely by the claims. Accordingly, the present invention is not limited to that precisely as shown and described.

The invention claimed is:

1. A kit for collecting a biological sample, the kit comprising:
    one or more identification labels, a sample collection device, one or more sample containers, each of the one or more sample containers comprise a container and a lid, and a collecting pouch;
    each of the one or more identification labels comprising one or more machine-readable codes with unique identification characteristics on one side and an adhesive on the other side;
    the sample collection device being configured to collect the biological sample from a sample source and dispense the biological sample into the one or more sample containers;
    each of the one or more sample containers being configured to receive therein the biological sample dispensed from the sample collection device; and
    the collecting pouch configured to secure the one or more sample containers for transportation; and
    wherein the sample collection device contains the one or more identification labels, the one or more sample containers and the collecting pouch within the sample collection device, the sample collection device configured with a removable seal that prevents access and removal of the one or more identification labels, the one or more sample containers, and the collecting pouch contained therein until the removable seal is pulled off.

2. The kit according to claim 1, wherein each of the one or more identification labels include serialized machine-readable codes in consecutive order that facilitate data reporting and tracking with respect to inventory usage.

3. The kit according to claim 1, wherein each of the one or more identification labels enables chain-of-custody procedures by tracking the one or more sample containers containing the biological sample.

4. The kit according to claim 1, wherein each of the one or more identification labels tracks a chronological record of the biological sample, identifying information of the originating source of the biological sample, identifying information of a donor of the biological sample, identifying information of an apparatus used to obtain the biological sample, identifying information of a location from where the biological sample was obtained, identifying information of each person who collected and/or handled the biological sample, and results obtained from analyzing the biological sample.

5. The kit according to claim 1, wherein the machine-readable code comprises a bar code, a matrix code or two-dimensional bar code, a radio frequency identification (RFID), a magnetic strip, a microchip, or an optical character recognition (OCR).

6. The kit according to claim 1, wherein each of the one or more identification labels is secured onto the lid of each of the one or more sample containers using the adhesive side, each of the one or more identification labels having one or more portions of the adhesive side that remain unassociated with the lid, the one or more unassociated portions of the adhesive side being covered with protective covering that can optionally comprise one or more tabs, the one or more unassociated portions being configured to affix to a side of a sample container from the one or more sample containers once the lid is secured to the sample container and the protective covering is removed from one or more unassociated portions of the adhesive side.

7. The kit according to claim 1, wherein each of the one or more sample containers comprises a locking mechanism that secures the lid to the container.

8. The kit according to claim 1, wherein the kit comprises one to five sample containers.

9. The kit according to claim 1, further comprising a cleaning wipe configured to be sealed within the sample collection device.

10. The kit according to claim 1, wherein the biological sample is urine, fecal matter, hair, blood, saliva, skin/epidermal cells, muscle, an internal organ, a plant material, or foodstuff.

11. A kit for collecting a biological sample, the kit comprising:
    one or more sample containers, each of the one or more sample containers composed of a malleable or pliable, non-elastic material, the one or more sample containers configured to receive and wrap or otherwise contain therein the biological sample;
    a sample shipping container comprises a sealing flap;
    one or more identification labels, the one or more identification labels each comprising a machine-readable code with unique identification characteristics on one side and an adhesive on the other side, each of the one or more identification labels is associated with the sealing flap as an integrated component; and
    a collecting pouch, the collecting pouch configured to contain the one or more sample containers, the sample shipping container, and the one or more identification labels,
    wherein the collecting pouch contains the one or more sample containers, the sample shipping container, and the one or more identification labels, the collecting pouch configured with a perforated top sealing the collecting pouch and prevent access and removal of the one or more sample containers, the sample shipping container, the one or more identification labels contained therein until the collecting pouch is opened.

12. The kit according to claim 11, wherein the one or more sample containers is a flat sheet of aluminum.

13. The kit according to claim 11, wherein the sample shipping container is an envelope, canister mailing pouch, or a mailing box.

14. The kit according to claim 11, wherein each of the one or more identification labels include serialized machine-readable codes in consecutive order that facilitate data reporting and tracking with respect to inventory usage.

15. The kit according to claim 11, wherein each of the one or more identification labels enables chain-of-custody procedures by tracking the one or more sample containers containing the biological sample.

16. The kit according to claim 11, wherein each of the one or more identification labels tracks a chronological record of the biological sample, identifying information of the originating source of the biological sample, identifying information of a donor of the biological sample, identifying information of an apparatus used to obtain the biological sample, identifying information of a location from where the biological sample was obtained, identifying information of each person who collected and/or handled the biological sample, and results obtained from analyzing the biological sample.

17. The kit according to claim 11, wherein the machine-readable code comprises a bar code, a matrix code or two-dimensional bar code, a radio frequency identification (RFID), a magnetic strip, a microchip, or an optical character recognition (OCR).

18. The kit according to claim 11, wherein the biological sample is hair, fecal matter, skin/epidermal cells, muscle, an internal organ, a plant material, or a foodstuff.

19. The kit according to claim 11, wherein the collecting pouch further comprises a zip-lock seal configured to reseal the collection pouch after the perforated top has been opened.

20. The kit according to claim 11, further comprising a cleaning wipe configured to be sealed within the sample collection device.

\* \* \* \* \*